United States Patent
Buchanan

(10) Patent No.: US 10,729,514 B2
(45) Date of Patent: Aug. 4, 2020

(54) SELF-HEATING ELECTRIC PLUGGER/SYRINGE NEEDLE FOR USE IN A ROOT CANAL

(71) Applicant: L. Stephen Buchanan, Santa Barbara, CA (US)

(72) Inventor: L. Stephen Buchanan, Santa Barbara, CA (US)

(73) Assignee: Dental Education Laboratories, Inc., Santa Barbara, CA (US)

( * ) Notice: Subject to any disclaimer, the term of this patent is extended or adjusted under 35 U.S.C. 154(b) by 0 days.

(21) Appl. No.: 15/781,240

(22) PCT Filed: Dec. 5, 2016

(86) PCT No.: PCT/US2016/064974
§ 371 (c)(1),
(2) Date: Jun. 4, 2018

(87) PCT Pub. No.: WO2017/096379
PCT Pub. Date: Jun. 8, 2017

(65) Prior Publication Data
US 2018/0353262 A1  Dec. 13, 2018

Related U.S. Application Data

(60) Provisional application No. 62/262,904, filed on Dec. 3, 2015.

(51) Int. Cl.
*A61C 5/55* (2017.01)
*A61N 1/32* (2006.01)

(52) U.S. Cl.
CPC . *A61C 5/55* (2017.02); *A61N 1/32* (2013.01)

(58) Field of Classification Search
CPC .... A61C 5/40; A61C 5/50; A61C 5/55; A61C 5/60–68; A61C 9/0026
See application file for complete search history.

(56) References Cited

U.S. PATENT DOCUMENTS

| | | | | |
|---|---|---|---|---|
| 5,752,825 | A | * 5/1998 | Buchanan | A61C 5/42 433/102 |
| 7,762,958 | B1 | * 7/2010 | Webler | A61B 90/06 600/549 |
| 2002/0142261 | A1 | 10/2002 | Van Den Houdt | |
| 2010/0209867 | A1 | 8/2010 | Becker et al. | |

* cited by examiner

*Primary Examiner* — Edward Moran
(74) *Attorney, Agent, or Firm* — Gable Gotwals

(57) ABSTRACT

A self-heating electric plugger/syringe needle (10/70) with the conductive element (50) on the external surface of the needle (10/70) is described. The needle (10/70), which can be divided into shank (30) and tip (20) portions, is hollow and is made of an electrically resistive material. A conductive element (50) located on the external surface of the needle runs along the length of its shank (30) and the length of its tip (20). An insulating material (60) located between the conductive element (50) and the external surface of the needle runs along the length of the shank (30). The conductive element (50) contacts the tip (20) of the needle, causing the needle to self-heat when electric current is supplied. A method for filling a root canal using the self-heating electric plugger/syringe needle (10/70) is also described.

16 Claims, 4 Drawing Sheets

SELF-HEATING ELECTRIC PLUGGER/SYRINGE NEEDLE FOR USE IN A ROOT CANAL

CROSS-REFERENCE TO RELATED APPLICATIONS

This United States application is the National Phase of PCT Application No. PCT/US2016/064974 filed 5 Dec. 2016, which claims priority to U.S. Provisional Patent Application No. 62/262,904 filed 3 Dec. 2015.

BACKGROUND OF THE INVENTION

This invention relates to dental implements and, more particularly to dental implements which are particularly designed for the filling of root canals with sealing materials.

There are several methods of sealing root canal systems, and most of them using a rubber-like material called gutta percha. This gutta percha may be in the form of a tapered cone, which is compacted into the root canal with pluggers. Alternatively, the gutta percha may be placed as a coating on an obturating carrier, which is warmed to soften the gutta percha, and deposited in the root canal where the carrier compacts the material into the canal space.

Currently, the shapes of filling materials and obturating carriers do not match the tapering shapes of prepared root canals. When the step-back technique of canal shaping is used, the final shape of the canal preparation can only be discerned indirectly by the increments that each larger instrument fits further back from the terminus of the canal, a difficult skill learned only after much experience. As the prepared taper is often obscure to the clinician, it is likewise difficult to pick an appropriately tapered gutta percha point or obturating carrier with which to seal the canal. If the selected obturating device or gutta percha point is too tapered, it will bind in the canal short of the canal's terminus, causing the crucial apical seal to be inadequate and allowing leakage and failure of the endodontic treatment. If the obturating device or gutta percha point is too narrow, little hydraulic pressure will be exerted on the filling material in the cervical two-thirds of the canal during condensation procedures and lateral or accessory canals in that region of the canal may not be sealed, again increasing the chance for failure of the endodontic treatment.

While there are many techniques of filling root canals, it is generally recognized in the field of endodontics that those methods which warm and soften the gutta percha filling material, thereby allowing it to be thoroughly compacted into all the nooks and crannies of root canal systems, are superior to those techniques which do not thermoplasticize the gutta percha prior to condensation.

Vertical condensation of warm gutta percha is a known technique for warming and compacting gutta percha in a root canal (see e.g. U.S. Pat. No. 5,406,053). In this technique, an appropriately tapered gutta percha cone is fit and cemented in the prepared root canal, and a flame-heated or electrically-heated gutta percha heat carrier is used to sear off the gutta percha cone at the orifice level of the canal. Pressing the softened gutta percha into the canal with an appropriately sized vertical condensation plugger initiates the first wave of condensation, filling any lateral canals present in that region in the primary canal. The heat carrier is then reintroduced into the canal in order to penetrate the gutta percha several millimeters (mm), heat the apical mass, and remove a portion of the apical mass so that the next wave of condensation may occur deeper in the root. These heating and compacting cycles continue until the final wave of condensation which ends approximately five to seven millimeters from the canal terminus.

It generally takes from three to seven waves of condensation to reach this end point. At the end point, the clinician must either place a retentive post in the coronal canal space or backfill it with gutta percha. Backfilling can be done by heating small pieces of gutta percha and sequentially packing them into the canal or by syringing alloquates of pre-heated gutta percha from a gutta percha gun and compacting them with pluggers. Downpacking with multiple waves of condensation and backfilling in the manners described require at least seven different instruments, fairly extensive training of the clinician and chairside assistant, and between fifteen and thirty minutes of clinical time. Furthermore, these condensation pluggers and heat carriers lack a correlating mechanism to match their sizes to the taper of the canal preparation.

In the preparation of a root canal by removing the pulp and shaping the canal to the best configuration for receiving filling materials, such as gutta percha, it is extremely important to control the depth of penetration of root canal files and to limit the depth of penetration to the root tip.

Obturation condensation devices, often referred to as pluggers or, if provided with heating elements as heat carrier/pluggers, are designed for the insertion and packing of tapered gutta percha cones into a previously prepared root canal. For example, U.S. Pat. No. 5,921,775, herein incorporated by reference, describes an endodontic treatment system in which the shaping instruments, irrigation cannulas, filling implements, and related materials are designed to safely create specific tapers in root canal preparation. All of the identified implements are designed with the same taper, preferably one which is greater than the standard ISO taper of 0.02 mm of taper/mm of flute length.

When an electric heat plugger is used to downpack or condense the thermo-plasticized gutta percha into the apical and lateral canal spaces, the gutta percha that moves along the side of the plugger is usually removed after the downpack is completed, leaving the coronal canal space empty. A second obturation device called a gutta percha backfilling syringe is required to backfill the empty space. Gutta percha backfilling syringe needles are typically made of sterling silver or a silver alloy because heat conduction from the syringe heating chamber to the end of the syringe needle must be adequate to keep the temperature of the gutta percha material high enough to remain thermo-plastic along the entire length of the needle to its tip. However, syringe needles made of silver or silver alloys lack the inherent rigidity to be used to condense the thermo-plasticized material into the root canal space after they have heated and extruded said material into the canal space.

As a result, there is a need for a backfilling syringe needle that can conduct heat from the syringe heating chamber to the tip of the needle while maintaining sufficient rigidity to pack the warmed gutta percha into the canal space. There is also a need for a needle that eliminates the need to fit tapered gutta percha master cones or carriers into the root canal and reduces the typical device set of a downpacking electric heat plugger and a gutta percha backfilling syringe into a single device.

SUMMARY OF THE INVENTION

A self-heating electric plugger/syringe needle with the conductive element on the external surface of the needle is described. The needle, which can be divided into shank and tip portions, is hollow and is made of an electrically resistive material. A conductive element located on the external surface of the needle runs along the length of its shank and the length of its tip. An insulating material located between the conductive element and the external surface of the needle runs along the length of the shank. The conductive element contacts the tip of the needle, causing the needle to self-heat when electric current is supplied. The conductive element may have a sinusoidal or straight-line pattern. A method for filling a root canal using the self-heating electric plugger/syringe needle is also described.

DETAILED DESCRIPTION OF THE PREFERRED EMBODIMENTS

Figure 1:
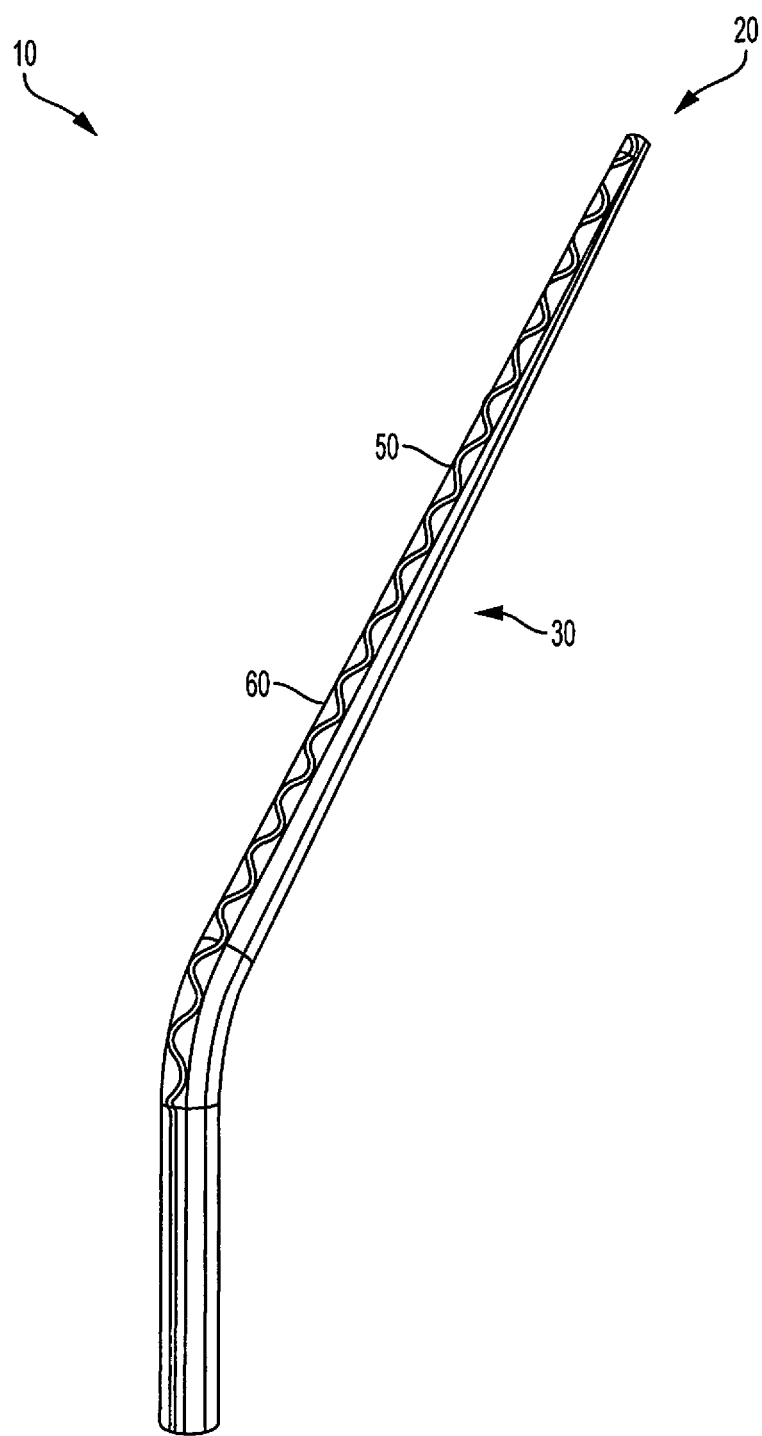
FIG. 1 is a side view of an embodiment of a self-heating electric plugger/syringe needle made according to this invention.
Figure 2:
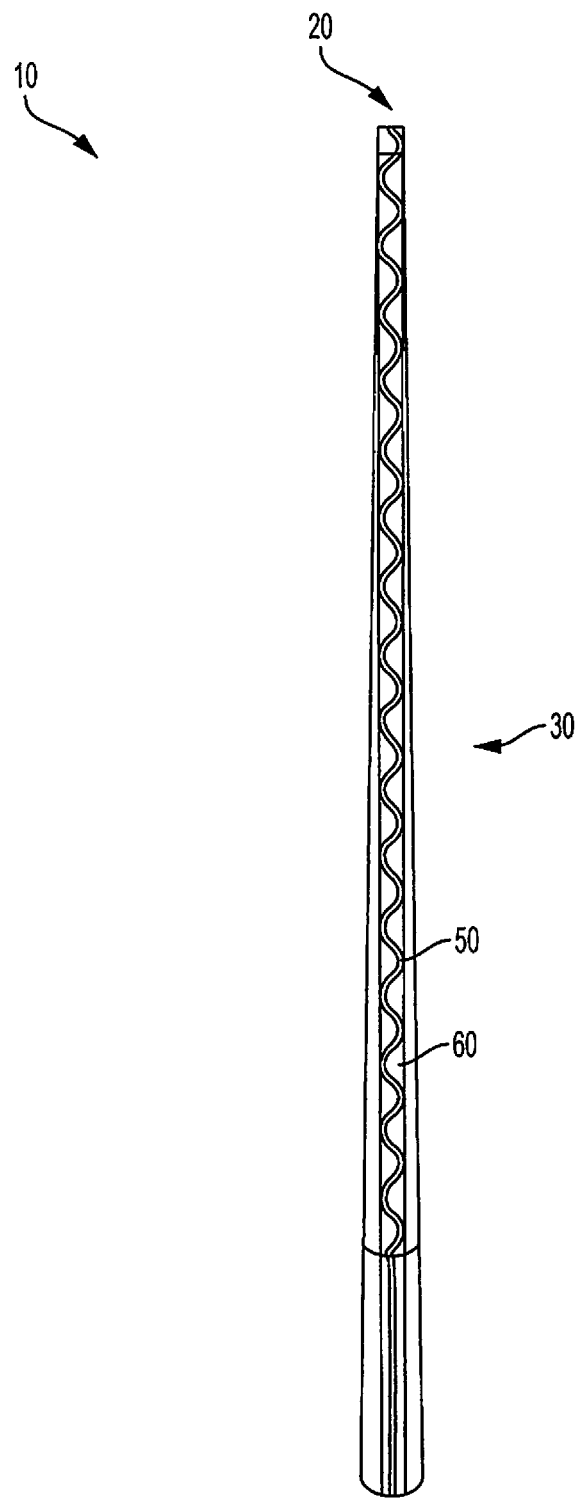
FIG. 2 is a top view of the embodiment shown in FIG. 1.
Figure 3:
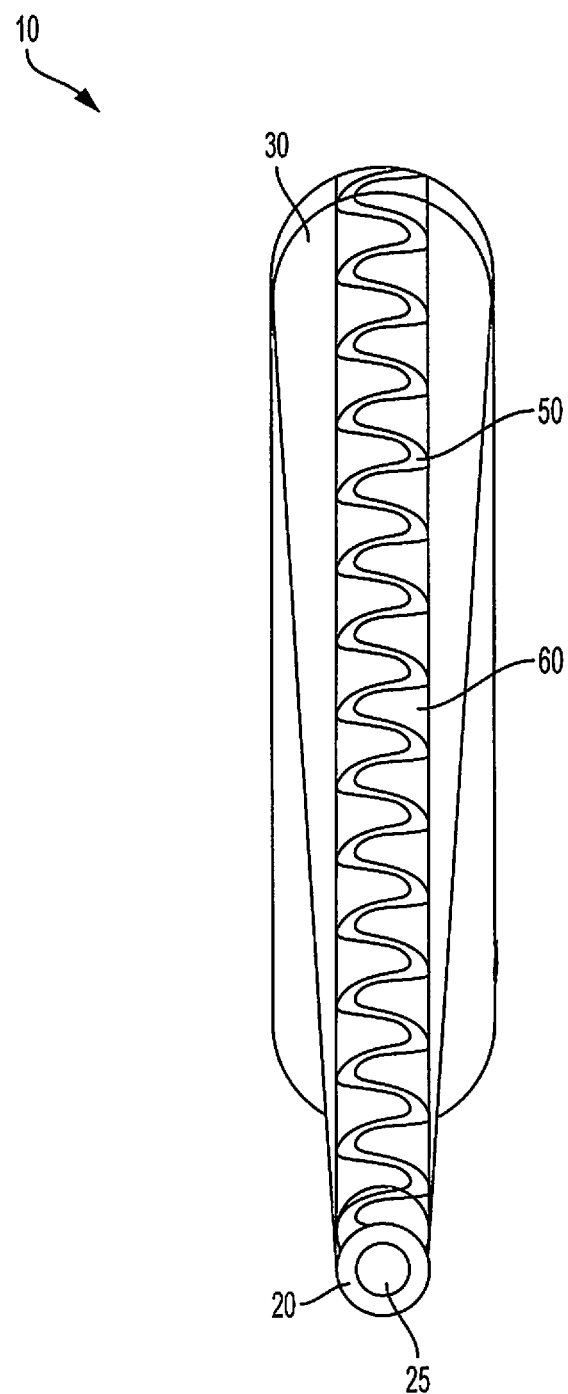
FIG. 3 is an enlarged view of the tip of the embodiment shown in FIG. 1.

As shown in FIGS. 1-3, the self-heating electric plugger/syringe needle 10 can be divided into a shank 30 portion and a tip 20 portion. The shank 30 may be tapered, with the diameter of the taper increasing as the distance from the tip 20 increases. The end of the shank 30 opposite the tip 20 may be connected to a handpiece (not shown) which delivers electric current to the conductive element 50 as well as providing a handle for the clinician to manipulate the electric heat plugger/syringe needle 10. The bore 25 of the needle 10 is hollow. A gutta percha syringe mechanism is located in the handpiece so as to pre-soften and push the thermo-plasticized filling material out through the hollow space 25 inside the plugger/syringe needle 10.

The self-heating electric plugger/syringe needle 10 is made of an electrically resistive material, preferably stainless steel. A sinusoidal-shaped conductive element 50, also known as a heating element, on the external surface of the needle 10 runs along the length of its shank 30 and the length of its tip 20. The conductive element 50 is separated from the surface of the needle 10 by an insulating material 60, which also runs along the length of the shank 30 of the needle 10. However, at the tip 20 of the needle 10, the conductive element 50 directly contacts the electrically resistive material of the needle 10 (i.e., the tip 20 is non-insulated). The electrically resistive material acts as a ground to the electric current which, because the electrically resistive material is more resistive to the current than the insulating material 60, causes the needle 10 to self-heat.

Figure 4:
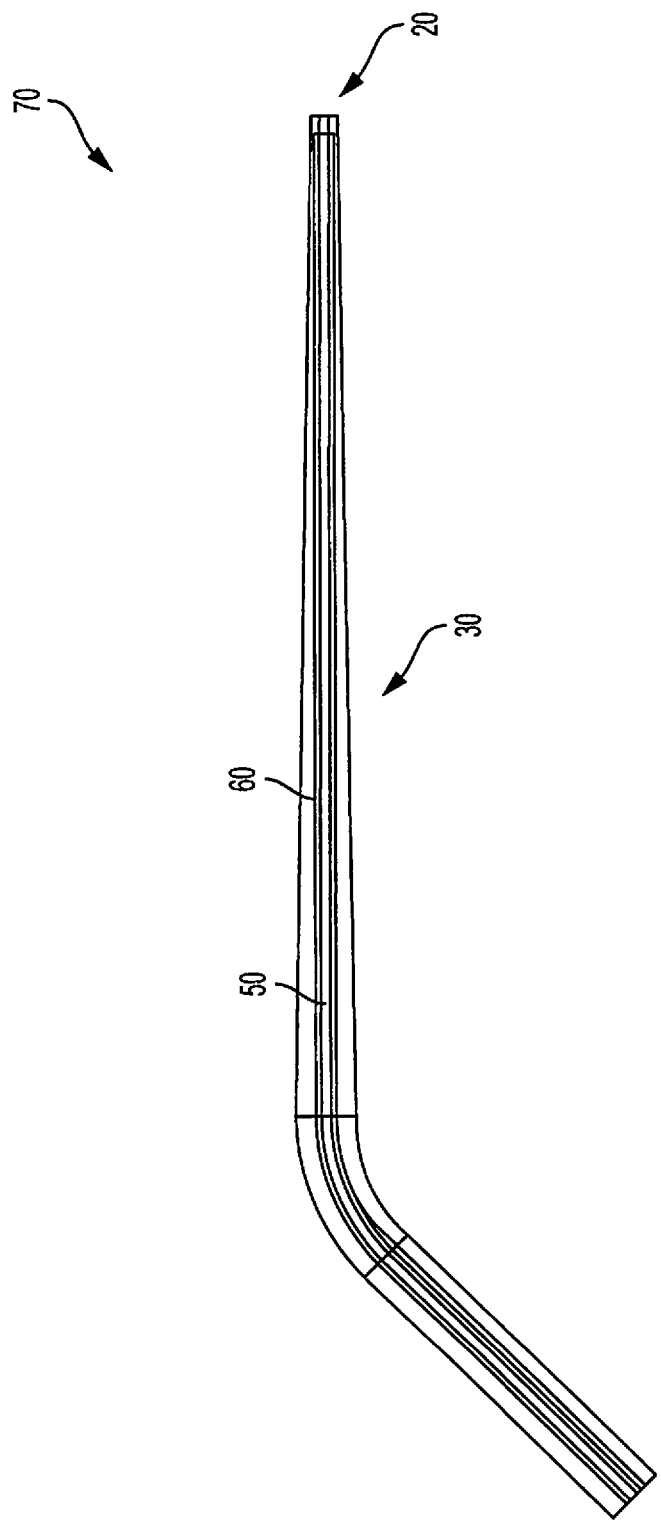
FIG. 4 is a side view of an alternative embodiment of a self-heating electric plugger/syringe needle made according to this invention.

As shown in FIG. 4, an alternative embodiment of the self-heating electric plugger/syringe needle 70 has a shank 30 portion and a tip 20 portion. The shank 30 may be tapered, with the diameter of the taper increasing as the distance from the tip 20 increases. The end of the shank 30 opposite the tip 20 may be connected to a handpiece (not shown) which delivers electric current to the conductive element 50 as well as providing a handle for the clinician to manipulate the electric heat plugger/syringe needle 70. The bore 25 of the needle 70 is hollow. A gutta percha syringe mechanism is located in the handpiece so as to pre-soften and push the thermo-plasticized filling material out through the hollow space 25 inside the plugger/syringe needle 70.

The self-heating electric plugger/syringe needle 70 is made of an electrically resistive material, preferably stainless steel. A conductive element 50, also known as a heating element, on the external surface of the needle 70 runs in a straight line along the length of its shank 30 and the length of its tip 20. The conductive element 50 is separated from the surface of the needle 70 by an insulating material 60, which also runs along the length of the shank 30 of the needle 70. However, at the tip 20 of the needle 70, the conductive element 50 directly contacts the electrically resistive material of the needle 70 (i.e., the tip is non-insulated). The electrically resistive material acts as a ground to the electric current which, because the electrically resistive material is more resistive to the current than the insulating material, causes the needle 70 to self-heat.

While self-heating electric plugger/syringe needles have been described with a certain degree of particularity, many changes may be made in the components of the needles, the construction and arrangement of those components, and methods of using the needles without departing from the spirit and scope of this disclosure. The invention, therefore, is limited only by the scope of the attached claims, including the full range of equivalency to which each element thereof is entitled.

What is claimed:

1. A dental self-heating electric needle comprising:
   an electrically resistive material extending from a tip at one end of the needle to a shank at an opposite end of the needle,
      the tip and the shank including a hollow bore configured to contain and dispense a thermo-plasticized filling material;
   the electrically resistive material surrounding the hollow bore; the electrically resistive material and the hollow bore extending an entire length of the needle;
   a conductive element located on an external surface of the needle and running along the entire length; and
   an insulating material located between the conductive element and the external surface of the needle,
   wherein the conductive element contacts the electrically resistive material of the needle at the tip portion, thereby heating the needle when electric current is supplied to the conductive element; and
   wherein during the heating the thermo-plasticized filling material exits the hollow bore at the one end and enters the hollow bore at the opposite end, and wherein the tip is flat and configured to dispense and down pack or condence the thermo-plasticized filling material into a root canal of a tooth.

2. A needle according to claim 1, wherein the conductive element has a sinusoidal pattern.

3. A needle according to claim 1, wherein the conductive element has a straight-line pattern.

4. A needle according to claim 1, wherein the electrically resistive material is stainless steel.

5. A dental self-heating electric needle comprising:
   an electrically resistive material extending from a tip at one end of the needle to a shank at an opposite end of the needle,
      the tip end and the shank including a hollow bore configured to contain and dispense a thermo-plasticized filling material;
   the electrically resistive material surrounding the hollow bore, the electrically resistive material and the hollow bore extending an entire length of the needle;

a conductive element extending the entire length; and
an insulating material;
a portion of the conductive element being isolated from the electrically resistive material of the needle by the insulating material,
the conductive element extending past an end of the insulating material to contact the electrically resistive material at the one end of the needle, and wherein the tip is flat and configured to dispense and down pack or condense the thermo-plasticized filling material into a root canal of a tooth.

6. A needle according to claim 5, wherein the conductive element has a sinusoidal pattern.

7. A needle according to claim 5, wherein the conductive element has a straight-line pattern.

8. A needle according to claim 5 further comprising the electrically resistive material including stainless steel.

9. A dental self-heating electric needle made of an electrically resistive material and comprising:
   a top at one end including a hollow bore configured to contain and dispense a thermo-plasticized filling material;
   a shank at the opposite end including the hollow bore;
   the hollow bore extending an entire distance between said ends;
   a conductive element located on an external surface of the needle and running the entire distance; and
   an insulating material located between the conductive element and the external surface of the needle;
   wherein the conductive element contacts the electrically resistive material of the needle at the one end, thereby heating the needle when electric current is supplied to the conductive element;
   wherein the thermo-plasticized filling material exits the hollow bore at the one end and enters the hollow bore at the opposite end, and wherein the tip is flat and configured to dispense and down pack or condense the thermo-plasticized filling material into a root canal of a tooth.

10. A needle according to claim 9, wherein the conductive element includes a sinusoidal pattern.

11. A needle according to claim 9, wherein the conductive element includes a straight-line pattern.

12. A needle according to claim 9 further comprising the electrically resistive material including stainless steel.

13. A dental self-heating electric needle made of an electrically resistive material and comprising:
   a tip at one end;
   a shank at the opposite end;
   a hollow bore extending an entire distance of the needle from the one end to the opposite end, the hollow bore configured to contain and dispense a thermo-plasticized filling material, wherein when in use the thermo-plasticized filling material enters the hollow bore at the opposite end and exits the hollow bore at the one end;
   a conductive element extending the entire distance of the needle and contacting the electrically resistive material at the one end;
   an insulating material located between the conductive element and the electrically resistive material needle up to, but not including, the one end, and wherein the tip is flat and configured to dispense and down pack or condense the thermo-plasticized filling material into a root canal of a tooth.

14. A needle according to claim 13, wherein the conductive element includes a sinusoidal pattern.

15. A needle according to claim 13, wherein the conductive element includes a straight-line pattern.

16. A needle according to claim 13 further comprising the electrically resistive material including stainless steel.

* * * * *